(12) United States Patent
Lee et al.

(10) Patent No.: US 6,780,179 B2
(45) Date of Patent: Aug. 24, 2004

(54) METHODS AND SYSTEMS FOR IN SITU TISSUE MARKING AND ORIENTATION STABILIZATION

(75) Inventors: Roberta Lee, Redwood City, CA (US); James W. Vetter, Portola Valley, CA (US); Ary S. Chernomorsky, Walnut Creek, CA (US)

(73) Assignee: Rubicor Medical, Inc., Redwood City, CA (US)

( * ) Notice: Subject to any disclaimer, the term of this patent is extended or adjusted under 35 U.S.C. 154(b) by 49 days.

(21) Appl. No.: 10/155,570

(22) Filed: May 22, 2002

(65) Prior Publication Data

US 2003/0220640 A1 Nov. 27, 2003

(Under 37 CFR 1.47)

(51) Int. Cl.[7] ............................................... A61B 18/18
(52) U.S. Cl. ........................................ 606/34; 606/159
(58) Field of Search ........................... 606/159, 27–52, 606/11–19, 170–171, 180

(56) References Cited

U.S. PATENT DOCUMENTS

| | | |
|---|---|---|
| 3,971,950 A | 7/1976 | Evans et al. |
| 4,130,112 A | 12/1978 | Frazer |
| 4,347,850 A | 9/1982 | Kelly-Fry et al. |
| 4,434,799 A | 3/1984 | Taenzer |
| 4,509,368 A | 4/1985 | Whiting et al. |
| 4,563,768 A | 1/1986 | Read et al. |
| 4,691,333 A | 9/1987 | Gabriele et al. |
| 4,829,184 A | 5/1989 | Nelson et al. |
| 5,009,660 A | 4/1991 | Clapham |
| 5,056,523 A | 10/1991 | Hotchkiss, Jr. et al. |
| 5,171,321 A | 12/1992 | Davis |
| 5,308,321 A | 5/1994 | Castro |
| 5,386,447 A | 1/1995 | Siczek |
| 5,409,497 A | 4/1995 | Siczek |
| 5,437,280 A | 8/1995 | Hussman |
| 5,451,789 A | 9/1995 | Wong et al. |
| 5,590,166 A | 12/1996 | Suni et al. |
| 5,590,655 A | 1/1997 | Hussman |
| 5,649,923 A | * 7/1997 | Gregory et al. ............... 606/15 |
| 5,660,185 A | 8/1997 | Shmulewitz et al. |
| 5,662,109 A | 9/1997 | Hutson |
| 5,702,405 A | 12/1997 | Heywang-Koebrunner |

(List continued on next page.)

FOREIGN PATENT DOCUMENTS

| | | |
|---|---|---|
| DE | 2610111 A1 | 9/1977 |
| DE | 4037387 | 5/1992 |
| GB | 1214707 A | 12/1970 |
| WO | WO 95/21582 | 8/1995 |
| WO | WO 00/08647 | 2/1999 |

*Primary Examiner*—Michael Peffley
*Assistant Examiner*—Pete Vrettakos
(74) *Attorney, Agent, or Firm*—Young Law Firm, P.C.

(57) ABSTRACT

A method of marking an orientation of a cut specimen of tissue prior to excision thereof from a body includes steps of disposing a tissue-marking probe in the body adjacent the cut specimen, the tissue-marking probe including a tissue-marking tool configured to selectively mark the cut specimen. A surface of the cut specimen is then marked with the tissue-marking tool such that the orientation of the cut specimen within the body is discernable after the cut specimen is excised from the body. The tissue-marking tool may be configured to selectively bow out of and back into a window defined near a distal tip of the probe and the marking step may include a step of selectively bowing the tissue-marking tool out of the window and following the surface of the cut specimen while rotating the probe. The tissue-marking tool may include an RF cutting tool and the marking step may include a step of coagulating or cauterizing a selected portion of the surface of the cut specimen with the RF cutting tool. Alternatively, the marking step may include a step of delivering dye onto selected portions of the surface of the cut specimen.

17 Claims, 7 Drawing Sheets

U.S. PATENT DOCUMENTS

| | | |
|---|---|---|
| 5,706,327 A | 1/1998 | Adamkowski et al. |
| 5,776,177 A | 7/1998 | MacWhinnie et al. |
| 5,805,665 A | 9/1998 | Nelson et al. |
| 5,810,742 A | 9/1998 | Pearlman |
| 5,820,552 A | 10/1998 | Crosby et al. |
| 5,855,554 A | 1/1999 | Schneider et al. |
| 5,860,934 A | 1/1999 | Sarvazyan |
| 5,868,673 A | 2/1999 | Vesly |
| 5,876,339 A | 3/1999 | Lemire |
| 5,879,357 A | 3/1999 | Heaton et al. |
| 5,899,865 A | 5/1999 | Chance |
| 5,902,310 A | 5/1999 | Foerster et al. |
| 5,997,509 A | 12/1999 | Rosengart et al. |
| 5,999,836 A | 12/1999 | Nelson et al. |
| 6,022,362 A * | 2/2000 | Lee et al. .................. 606/159 |
| 6,056,700 A * | 5/2000 | Burney et al. ............... 600/564 |
| 6,068,638 A | 5/2000 | Makeower |
| 6,077,231 A | 6/2000 | Milliman et al. |
| 6,152,899 A * | 11/2000 | Farley et al. ................ 604/113 |
| 6,220,248 B1 * | 4/2001 | Voegele et al. ............ 1128/898 |
| 6,432,064 B1 * | 8/2002 | Hibner et al. ............... 600/564 |
| 6,440,147 B1 * | 8/2002 | Lee et al. ................... 606/159 |
| 6,454,727 B1 * | 9/2002 | Burbank et al. ............. 600/567 |
| 6,517,498 B1 * | 2/2003 | Burbank et al. ............. 600/564 |
| 6,540,695 B1 * | 4/2003 | Burbank et al. ............. 600/564 |
| 6,626,903 B2 * | 9/2003 | McGuckin et al. ........... 606/45 |
| 6,638,273 B1 * | 10/2003 | Farley et al. ................. 606/27 |
| 6,689,145 B2 * | 2/2004 | Lee et al. ................... 606/159 |
| 6,702,831 B2 * | 3/2004 | Lee et al. ................... 606/159 |

\* cited by examiner

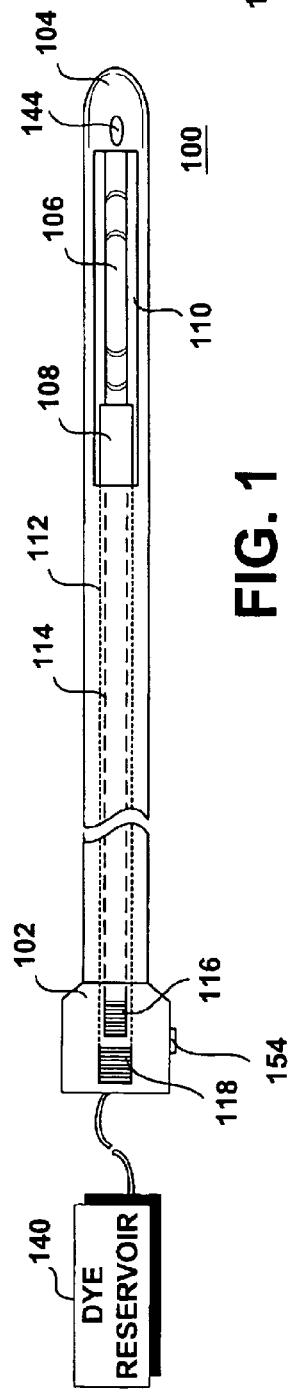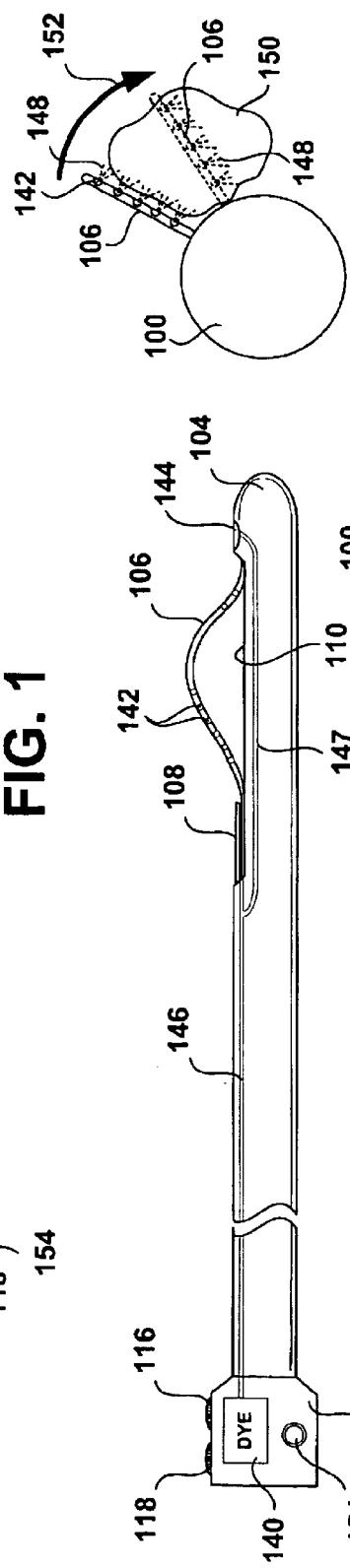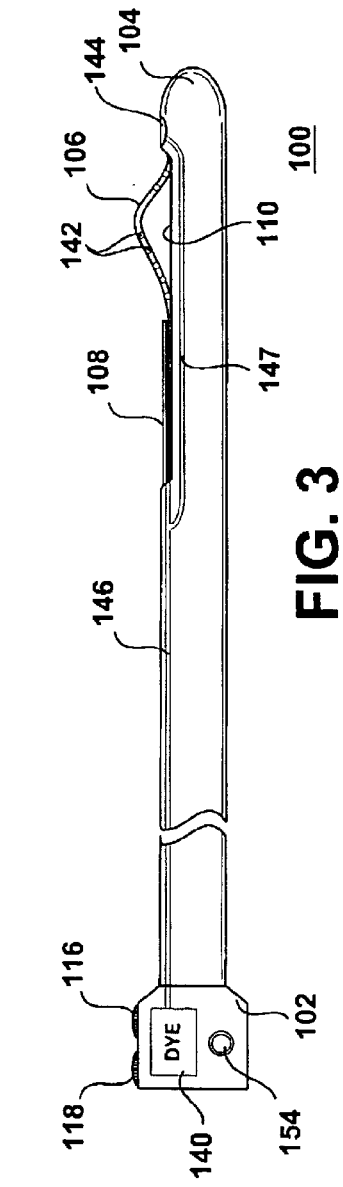

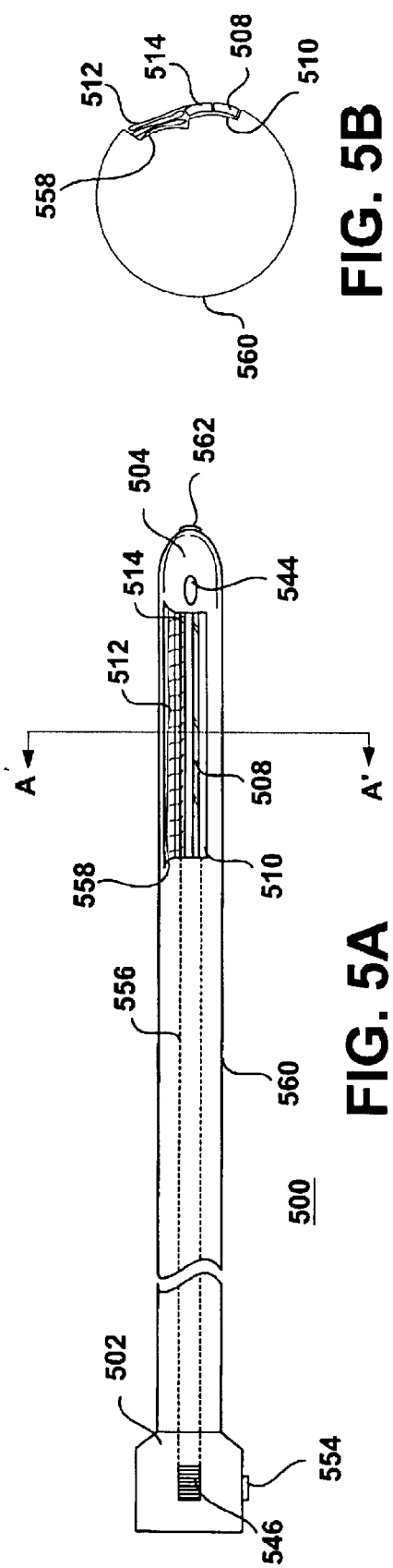
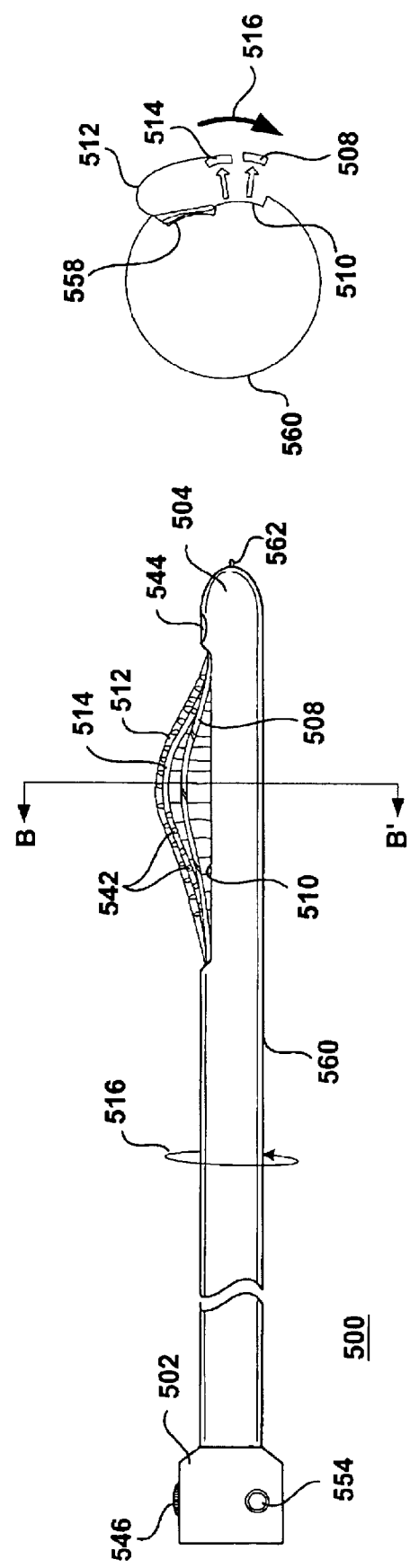

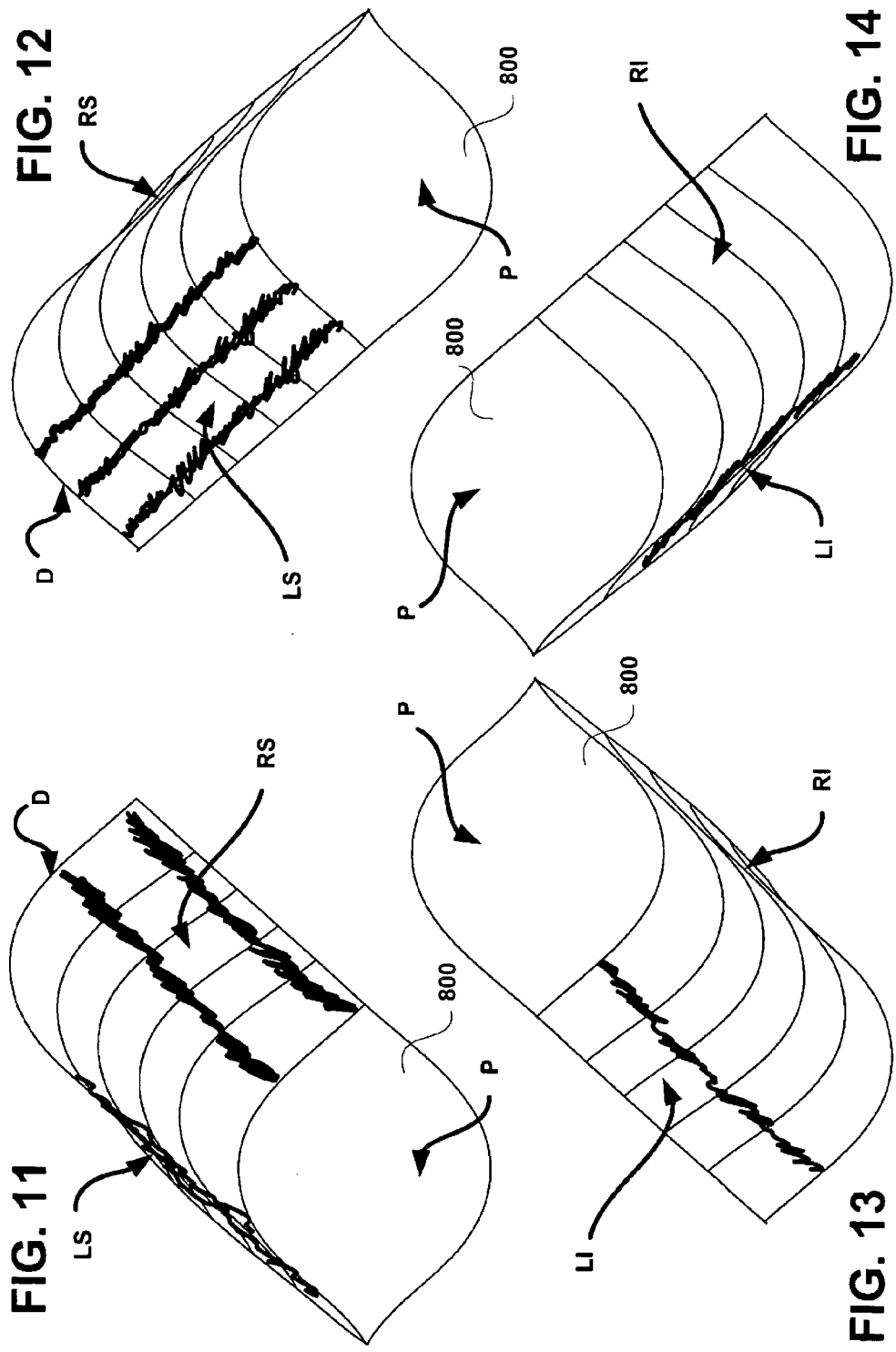

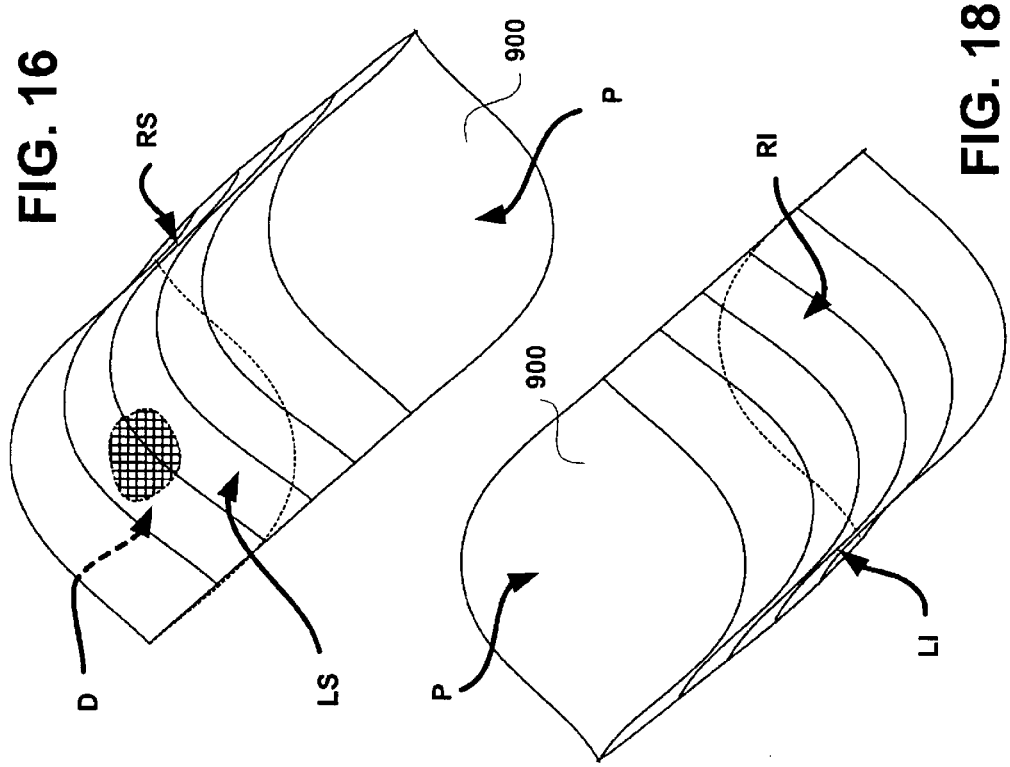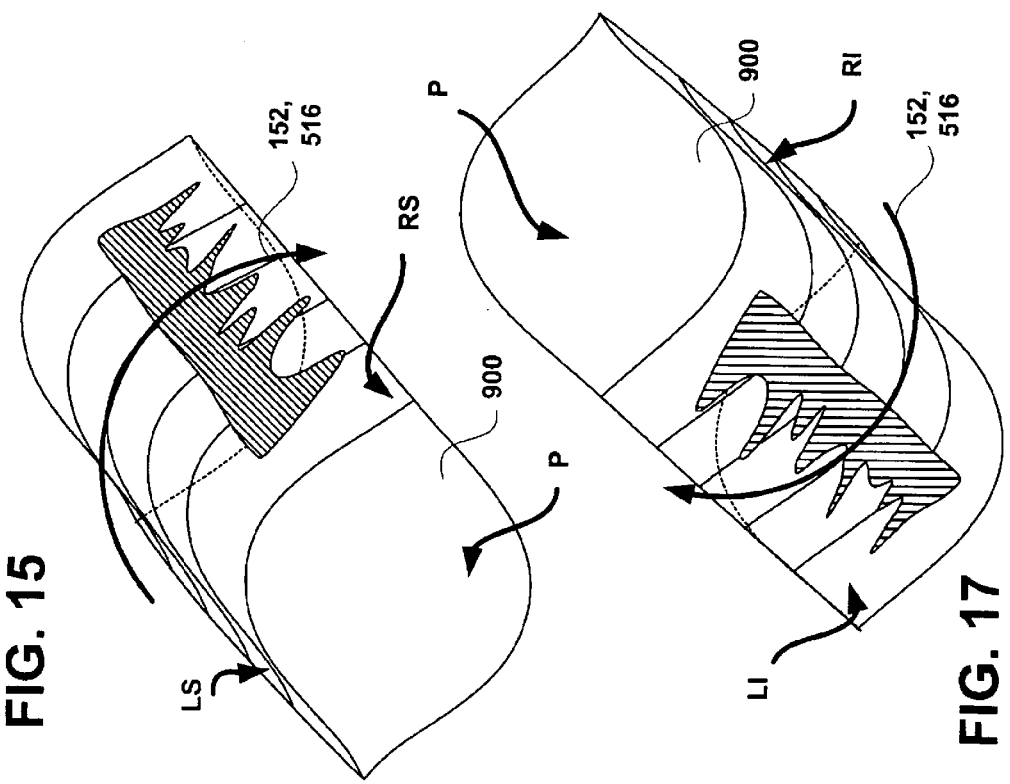

METHODS AND SYSTEMS FOR IN SITU TISSUE MARKING AND ORIENTATION STABILIZATION

BACKGROUND OF THE INVENTION

1. Field of the Invention

The present invention relates to the marking of soft tissue specimens to preserve or reconstruct the orientation of a soft tissue specimen after the specimen is removed from the patient's body.

2. Description of the Related Art

The marking of a biopsy specimen to indicate the orientation of the specimen within the body may be crucial for later treatment. For example, knowledge of the exact orientation of a biopsy specimen of breast tissue is an important aspect of any breast conserving therapy for breast cancer. A proper biopsy should have good margins of normal, uninvolved breast tissue surrounding the cancerous lesion within the breast. If a margin is "dirty" (close to or involved with the lesion), the risk of recurrence of the cancer increases. What distance actually constitutes a good margin remains controversial. Large margins are safest, but may result in an overly large cavity within the breast, which may result in a less than satisfactory cosmetic result. Smaller margins, on the other hand, result in smaller cavities within the breast, but increase the risk that some of the cells on the periphery of the margin will be found to be involved in the lesion. Moreover, smaller margins may increase the risk of seeding cancerous cells within the breast. For example, 1 cm margins are universally accepted as safe, while some favor the excision of specimens with margins of as little as 1 mm. The National Surgical Adjuvant Breast and Bowel Project (NSABP), the major study group for breast treatment, has previously endorsed a margin equal to one normal cell between the cancer and the cut edge of the specimen. The mainstream approach, however, appears to call for 5 mm to 10 mm margins between the cancerous lesion and the cut edge of the specimen. Except for some women with Ductal Carcinoma In Situ (DCIS), women who undergo biopsies with such margins will also receive post-operative radiation therapy to treat any remaining cancer within the breast.

Best practices indicate that the biopsy specimen should be marked after removal thereof form the patient, in case one or more cut surfaces contain tumor or are close to the tumor. If the surgeon learns from the pathologist that the inferior margin is "positive", the he or she will take the patient back to the operating room and excise additional tissue from the inferior aspect of the cavity. If the specimen is not adequately marked, then tissue from the entire cavity must be excised. This may lead to the unnecessary excision of a vast amount of normal breast tissue, leading to an unsatisfactory cosmetic result. For at least these reasons, specimen marking for orientation is essential and should be an integral part of any breast (or any other soft tissue) cancer treatment protocol.

Many surgeons mark the excised specimen by sewing a suture onto different sides of the specimen (usually two or three sides). An example of such marking would be a short suture to mark the superior aspect of the specimen, a long suture to mark the lateral aspect thereof and a suture with short and long tails to mark the deep aspect of the specimen. If the surgeon determines that a radiograph or an X-ray is needed to confirm that the excised specimen contains suspicious microcalcifications, the specimen may be sent to a radiology department before the pathologist receives the specimen. The specimen is then typically flattened between two parallel plates to take the radiograph. This completely distorts the specimen, and it will never return to its original shape. This distortion renders the reconstruction of the specimen orientation difficult. For example, after a flattened specimen is returned to the surgeon, the sutures for the superior and lateral aspects may appear on the same side of the specimen.

A second and better way to mark specimens is to mark each side of the excised specimen (6 sides total) with a different color of stain. In this manner, if the specimen is distorted following a radiograph, the colored stain will still dictate the original orientation of the excised specimen within the surrounding tissue.

When a tissue specimen is removed from the breast, it should be removed without disturbing its original orientation within the breast. However, during the actual excision when the specimen is still within the breast, it may twist and/or turn, which changes its orientation even before it is removed. Thus, marking a specimen after removing it from the patient may not preserve the original orientation of the specimen. Therefore, even conscientious marking of an excised specimen may not preserve the true orientation of the lesion within the surrounding tissue. In turn, such marking may lead to confusion, misinformation and ultimately may result in a less than optimal treatment of the patient.

What are needed, therefore, are improved methods and systems for tissue marking. What are also needed are methods, systems and devices for preserving the orientation of tissue specimens.

SUMMARY OF THE INVENTION

It is, therefore, an object of the present invention to provide methods and systems for tissue marking. It is another object of the present invention to provide methods, systems and devices for preserving the orientation of tissue specimens.

In accordance with the above-described objects and those that will be mentioned and will become apparent below, a method of marking an orientation of a cut specimen of tissue prior to excision thereof from a body, includes steps of disposing a tissue-marking probe in the body adjacent the cut specimen, the tissue-marking probe including a tissue-marking tool configured to selectively mark the cut specimen and marking a surface of the cut specimen with the tissue-marking tool such that the orientation of the cut specimen within the body is discernable after the cut specimen is excised from the body.

The tissue-marking tool may be configured to selectively bow out of and back into a window defined near a distal tip of the probe and the marking step may include a step of selectively bowing the tissue-marking tool out of the window and following the surface of the cut specimen while rotating the probe. The disposing step may dispose the tissue-marking probe directly within the tissue. The disposing step may dispose the tissue-marking probe within a cannula disposed adjacent the cut specimen. The tissue-marking tool may include an RF cutting tool and the marking step may include a step of coagulating a portion of the surface of the cut specimen with the RF cutting tool. The coagulating step may include a step of momentarily increasing an RF power delivered to the portion of the surface of the cut specimen by the RF cutting tool. Alternatively, the coagulating step may include a step of momentarily maintaining the RF cutting tool substantially immobile on the portion of the surface of the specimen while the RF power delivered to the RF cutting tool is maintained constant.

The marking step may include a step of delivering dye onto the surface of the cut specimen. The dye may include, for example, Methylene Blue, Congo Red and/or Lymphazurin® Blue. The marking step may include delivering a first dye of a first color to a first portion of the surface of the cut specimen and delivering a second dye of a second color to a second portion of the surface of the cut specimen. The first portion may include a proximal and/or a distal end of the cut specimen. The dye-delivering step may deliver the dye at a selectable graduated rate to the surface of the specimen. In this manner, the dye may be delivered darker to a first portion of the surface of the specimen and may be delivered relatively lighter to a second portion of the surface of the specimen.

The present invention is also a soft tissue excisional method, comprising the steps of disposing a probe within tissue from which a tissue specimen may be to be taken, the probe including an RF tissue cutting tool configured to selectively bow out of and back into a window defined near a distal tip of the probe; rotating the probe while applying RF energy to the RF cutting tool and selectively bowing the cutting tool out of the window to cut the specimen from the tissue and selectively coagulating selected portions of a surface of the specimen with the RF cutting tool such by that the orientation of the specimen within the body may be discernable after the cut specimen may be excised from the body.

The method may further include a step of isolating the cut specimen from surrounding tissue by at least partially encapsulating the cut specimen with a thin flexible film deployed in a path of the RF cutting tool.

The present invention is also an intra-tissue therapeutic device, comprising a probe body, the probe body defining at least one internal dye lumen and a first window near a distal tip of the probe body, and a tissue-marking tool configured to selectively bow out of and back into the first window, the tissue-marking tool defining at least one dye port in fluid communication with the at least one dye lumen.

The device may further include one or more dye reservoirs in fluid communication with one or more dye lumens internal to the probe body. The dye reservoirs may be disposed within the probe body or external thereto. The probe body further may include a tissue-cutting tool. The tissue-cutting tool may be configured to selectively bow out and back into the probe body and the tissue-marking tool may be configured to follow in a path of the tissue-cutting tool as the device is rotated. The tissue-cutting tool may bow out and back into the first window. The probe body may define a second window near the distal tip thereof and the cutting-tool may be configured to selectively bow out of and back into the second window. The distal tip may define a distal dye port, the distal dye port being in fluid communication with the internal lumen(s). The devices disclosed herein may be configured for a single use and may be disposable. The dye reservoir(s) may be pre-loaded with a dye, such as, for example, Methylene Blue, Congo Red and/or Lymphazurin® Blue. The cutting tool may include an RF cutting tool and may further include a distal RF tissue-cutting tool disposed in the distal tip of the probe body.

A specimen isolator may be coupled to the tissue-marking tool, the specimen isolator being adapted to isolate the specimen from tissue surrounding the specimen. The specimen isolator may include a thin flexible film of material, one end thereof being attached to the probe body and another end thereof being attached to the tissue-marking tool. The material of the tissue isolator may be selected from a group including a polyorganosiloxane, a polydiorganosiloxane, an inorganic elastomer, a silicone elastomer, a teraphthalate, a tetrafluoroethylene, a polytetrafluoroethylene, a polyimid, a polyester, Kevlar® and/or M5®, for example. The specimen isolator may be configured to extend radially from the probe body out of the window when the tissue-marking tool is bowed.

The present invention is also an intra-tissue therapeutic device, comprising a probe body, the probe body defining an internal tool lumen that emerges from the probe body at a tool port defined near a distal tip of the probe body; a tool actuator, and a tissue specimen stabilization tool mechanically coupled to the tool actuator, the stabilization tool including a barbed tip adapted to selectively slide within the tool lumen and extend out of the tool port to penetrate and stabilize tissue adjacent the tool port.

The internal tool lumen may be generally parallel to a longitudinal axis of the probe body near a proximal end thereof and the internal tool lumen may then curve away from the axis near the distal tip of the probe body to emerge at the tool port. A cutting tool may be disposed near the tip of the probe body. The cutting tool may include an RF cutting element that selectively bows out of and back into a window defined in the probe body, the RF cutting element being adapted to cut a volume of revolution of tissue as the probe body is rotated inside a patient's soft tissue. The barbed tip may be configured to expand when emerging from the tool port. The device may be configured for a single use and may be disposable.

The present invention may also be viewed as a soft tissue intra-tissue therapeutic device, comprising a cutting tool adapted to cut a specimen from surrounding tissue; a tissue-marking tool adapted to mark the specimen, at least a portion of the marking tool being mechanically coupled to the cutting means, and a tissue isolator, the tissue isolation means being adapted to expand radially form the device and isolate the cut specimen from the surrounding tissue as the device may be rotated.

The cutting tool may include a radio frequency (RF) cutting tool. The RF cutting tool may include a distal RF cutting tool disposed at a distal tip of the device. The RF cutting tool may be configured to selectively bow out of and back into a body of the device to cut a volume of revolution of tissue as the device is rotated inside within the tissue. The tissue-marking tool may also be configured to deliver dye to a selected portion of a surface of the cut specimen. The tissue-marking tool may be configured to selectively bow out of and back into a body of the device and to follow a path of the cutting tool as the device may be rotated. The tissue isolator may include a thin flexible film of material, one end of the film being attached to a body of the device and another end thereof being attached to the tissue-marking tool. Means for delivering a pharmaceutical agent to the surrounding tissue may also be included, as may means for suctioning smoke, blood and/or bodily fluids.

BRIEF DESCRIPTION OF THE DRAWINGS

FIG. 1 shows a top view of a tissue-marking device according to an embodiment of the present invention.

FIG. 2 shows the tissue-marking device of FIG. 1 in a first deployed configuration.

FIG. 3 shows the tissue-marking device of FIG. 1 in a second deployed configuration.

FIG. 4 shows a front view of the tissue-marking device of FIG. 1, to illustrate the operation of the tissue-marking probe.

FIG. 5A shows another embodiment of the present invention, in which an intra-tissue probe includes integrated specimen cutting, marking and isolation tools.

FIG. 5B shows a cross-section of the intra-tissue probe of FIG. 5A, taken along lines AA'.

FIG. 6A shows the intra-tissue probe of FIG. 5A, in which the specimen cutting, marking and isolation tools are shown in a deployed configuration.

FIG. 6B shows a cross section of the intra-tissue probe of FIG. 6A, taken along lines BB'.

FIG. 11 is a representation of a coagulation-marked tissue specimen, according to an embodiment of the present invention.

FIG. 12 is a representation of the marked tissue specimen of FIG. 11, viewed from another orientation.

FIG. 13 is a representation of the marked tissue specimen of FIG. 11, viewed from another orientation.

FIG. 14 is a representation of the marked tissue specimen of FIG. 11, viewed from another orientation.

FIG. 15 is a representation of a dye-marked tissue specimen, according to another embodiment of the present invention.

FIG. 16 is a representation of the marked tissue specimen of FIG. 15, viewed from another orientation.

FIG. 17 is a representation of the marked tissue specimen of FIG. 15, viewed from another orientation.

FIG. 18 is a representation of the marked tissue specimen of FIG. 15, viewed from another orientation.

DESCRIPTION OF THE INVENTION

Figure 7:
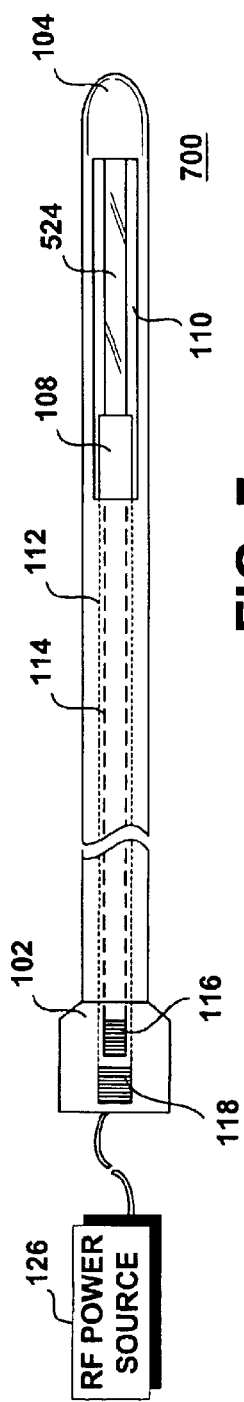
FIG. 7 shows an intra tissue probe for cutting and marking tissue specimens, according to another embodiment of the present invention.

FIG. 1 shows a top view of a tissue-marking device according to an embodiment of the present invention. The tissue-marking device 100 includes a proximal portion 102 and a distal tip 104. The proximal portion 102 may include a marking tool actuator 118 and the distal tip 104 may include a tissue-marking tool 106, which may include a thin flexible hollow ribbon or a thin flexible tube. The marking tool 106 may be configured to selectively bow out of and to retract within a window 110 defined within the body of the probe 100 when the marking tool actuator 118 is activated.

The tissue-marking probe 100 may also include an internal guide 112 (or may define an internal lumen) to enable the marking tool 106 to slide within the removable cutting probe 100 when marking tool actuator 118 is activated. The marking tool actuator 118 is shown as a thumb-activated dial in FIGS. 1–3 and 7–9. However, any other means of advancing and retracting the marking tool 106 may also advantageously be used within the context of the present invention. The tissue-marking probe 100 may further include a window slide 108 disposed within the window 110. The proximal end 102 of the probe 100 may further include window slide extending means 116. The window slide 108 is mechanically coupled to the window slide extending means 116 and is guided within the tissue-marking probe 100 by an internal guide or lumen 114 defined along the length of the probe 100. According to the present invention, the window slide 108 is configured to selectively cover a portion of the window 110 when the window slide extending means 116 are activated. Functionally, the window slide 108 covers a portion of the window 110 to selectively vary the size of the window 110 through which the tissue-marking tool 106 is allowed to extend or bow.

FIG. 2 shows a side view of the tissue-marking 100 probe of FIG. 1. As shown therein, the probe 100 is in a configuration wherein the tissue-marking tool 106 is in a bowed or extended state. As shown at 146, the body of the probe 100 may internally define at least one internal dye lumen 146 that is in fluid communication with a dye reservoir 140, which may be external to the probe 100 as shown in FIG. 1 or internal thereto, as shown in FIGS. 2 and 3. The dye reservoir 140 is adapted to contain a volume of at least one dye. The dye reservoir 140 is in fluid communication with the internal dye lumen 146, so as to deliver dye from the dye reservoir 140 to the tissue-marking tool 106. As shown, the tissue-marking tool 106 defines at least one dye port 142. Each of the dye ports 142 is in fluid communication with the dye lumen(s) 146 defined within the probe 100. A marking actuator 154 controls the flow of dye from the dye reservoir 140 to the dye ports 142. The marking actuator 154 may include a simple on/off valve to selectively open and cut the flow of dye to the dye ports 142. Alternatively, the marking actuator 154 may be pressure sensitive, so as to allow the physician to manually vary the flow of dye through the ports 142 by varying the pressure applied to the marking actuator 154. The probe 100 may also define a distal dye extrusion port 144 in fluid communication with the internal lumen 146 and the dye reservoir 140 (through a tributary lumen 147 defined within the probe body, for example).

FIG. 3 shows the probe 100 of FIG. 2 in a configuration wherein the window slide 108 is slid over a greater portion of the window 110 than is the window slide 108 of FIG. 2. In so doing, the window slide 108 effectively decreases the size (shortens the length) of the window 110 from which the tissue-marking tool 106 may bow or extend. Carefully choosing the extend to which the window slide 108 covers the window 110 allows precise control over the shape of the tissue-marking tool 106 as it bows or extends from the window 110. In turn, precise control over the shape of the tissue-marking tool 106 as it bows out from the window 110 allows the physician to precisely control the manner in which the tissue specimen is marked, as the tissue-marking tool 106 is caused to closely conform to the shape and size of the cut specimen.

FIG. 4 shows a front view of the probe 100 of FIGS. 1, 2 and 3 and illustrates the operation of the tissue-marking probe 100. As shown therein, the probe 100 is inserted into the patient's tissue, preferably following the insertion track of the excisional device that cut the specimen (shown at 150 in FIG. 4) from the surrounding tissue. Suitable excisional devices are disclosed, for example, in commonly assigned U.S. Pat. No. 6,022,362, the disclosure of which is incorporated herein by reference in their entireties. Alternatively, a split introducer (not shown) may be used to insert the probe 100 into the patient's soft tissue. The probe 100 is then navigated so that the window 110 is adjacent the cut specimen 150 to be marked. While rotating the probe body, in a clockwise direction (for example) as shown by the arrow 152, the tissue-marking tool 106 is extended radially out from the window 110 so as to encompass the previously cut specimen 150. Using the marking actuator 154, the physician causes dye 148 to extrude or spray out of the dye extrusion ports 142 and onto the cut specimen 150. The flow of dye 148 may be selectively cut on and off on different surfaces of the cut specimen 150 as the probe is rotated, so as to appropriately mark the orientation of the specimen 150 within the surrounding tissue. For example, the physician may mark (apply dye to) a left superior portion of the surface of the specimen 150, a right inferior portion thereof and the distal end of the specimen 150 (using the distal dye port 144, for example). In this manner, the physician may readily reconstruct the orientation of the specimen within the cavity created by the excision of the specimen 150.

As shown in FIGS. 5A, 5B, 6A and 6B, the tissue specimen, according to the present invention, may be simultaneously cut, marked and isolated from the surrounding tissue, all prior to retraction thereof from the patient. As shown in FIG. 5, the probe 500 may include a specimen isolator 512 attached to the tissue-marking tool 514. According to the present invention, the specimen isolator 512 is adapted to isolate the specimen from the surrounding tissue, as soon as the specimen is cut by the tissue-cutting tool 508. According to the present invention, the tissue-cutting tool 508 may include an RF blade or wire and may be a monopolar or bipolar RF cutting blade or wire. Additionally, the probe 500 may include a distal RF tissue-cutting tool 562 disposed in the distal tip 504 of the probe body 560. The tissue-cutting tool 508 may be configured to selectively bow out of and back into the same window 510 as the tissue-marking tool 514 bows out of and back into (as shown in FIGS. 5 and 6) or may be configured to bow out of and back into a separate window (not shown) defined within the body of the probe 500.

According to an embodiment of the present invention, the specimen isolator 512 may include a thin flexible film of material. One end of the film may be attached to the body 560 of the probe 500 and another end of the film may be attached to the tissue-marking tool 514. The specimen isolator 512, in this manner, is configured to extend radially from the probe body 560 out of the window 510 when and as the tissue-marking tool 514 is bowed. When the tissue-cutting tool 508 and the assembly including the tissue-marking tool 514 and the specimen isolator 512 are actuated by the same tool actuator 546, the probe 500 may cut and isolate the soft tissue specimen from the surrounding tissue with ease.

The tissue isolator 512, according to an embodiment of the present invention, may initially be stowed in a flattened configuration (best shown in FIG. 5B) in a recessed portion 558 defined within the body 560 of the probe 500. A weak and biologically inert adhesive may be used keep the specimen isolator 512 in its initially flattened state prior to deployment of the marking tool 514 within the patient's tissue. As the marking tool 514 is bowed out of the window 510 defined in the probe body 560, the specimen isolator 512 attached thereto unfolds from the recessed portion 558 and at least partially encapsulates the specimen as it is cut, as shown at FIG. 5B. Alternatively, the cutting tool 508 may be deployed independently of the tissue-marking tool 514—specimen isolator 512 combination. In that case, a complete cut of the specimen may be made within the patient prior to a subsequent tissue isolation and marking operation by an also independently actuated tissue-marking tool 514 and specimen isolator 512. One or more guides or internal lumens 556 may be defined within the probe body 560 to guide the tissue-marking tool 514 and/or the tissue-cutting tool 580. As the tissue-marking and cutting tools 514, 508 are constrained in their path along the length of the probe 500 and attached at their distal ends to or near the distal tip 504 of the probe 500, when the tools 514, 508 are pushed in the distal direction, they tend to bow out of the window 510, which provides the only outlet for such bowing.

Functionally, when the probe 500 is inserted into soft tissue and rotated (in the direction of arrows 516, for example), the cutting tool 508 may be caused to bow out of and to extend outwardly from the window 510 when actuated by the tool actuator 546 and caused to cut tissue coming into contact therewith. As the probe 500 rotates and cuts, the specimen isolator and the tissue-marking tool 514 may also be correspondingly deployed by the same (or a separate) tool actuator 546 and caused to precisely follow the trailing edge of the cutting tool 508 (thereby following in its path) as it cuts the soft tissue. During the cutting and specimen isolation procedure, the marking actuator 554 may be selectively actuated by the physician to mark the tissue specimen with dye from the dye extrusion ports 542 as it is being isolated. The probe 500 may also advantageously include a distal dye port 544 to mark the distal end of the specimen. As with the embodiments shown in FIGS. 1–3, a dye reservoir 140 may be disposed within the proximal end of the probe 500 or may be disposed external thereto. A suitable biologically inert propellant may also be present in the dye reservoir 140 to insure that the dye is appropriately sprayed onto the specimen to be marked. Suitable propellants include, for example, carbon dioxide and XXX. Several dye reservoirs 140 may be used to spray dyes of different colors onto the specimen. In that case, each color of dye may be delivered to all or selected ones of the dye ports 142 through a separate lumen defined within the probe body 560.

After the cutting, marking and/or isolating procedures are concluded, the probe 500 may then be safely retracted from the patient's soft tissue (such as the breast, for example). As the cut specimen is physically isolated from the remaining tissue mass, the probability of seeding the surrounding tissue with potentially abnormal cells is markedly decreased. This probability is also further decreased, as the probe 500 according to the present invention allows the surgeon to obtain adequate margins of healthy tissue surrounding the target lesion by choosing the degree of bowing and extension of the cutting tool 508 under (external or intra-tissue ultrasonic guidance, for example). In this manner, the integrity of the lesion itself is not violated, thereby maintaining tissue architecture intact.

As the tissue isolator 512 is preferably formed of a thin and flexible film, it is able to lay substantially flat against the outer surface of the probe body 500 or within a slightly recessed portion 558 of the probe body 500. The tissue isolator 512, therefore, offers little additional drag and resistance to the probe 500 as it is inserted into the incision made in the patient's skin during or prior to the procedure.

The material for the tissue isolator 512 may be a flexible semi-porous or non-porous material. For example, the tissue isolator may include a synthetic polymer such as a polyorganosiloxane or a polydiorganosiloxane. The material may include an inorganic elastomer, such as a silicone elastomer.

The tissue isolator may also include a teraphthalate (PET), a tetrafluoroethylene (TFE) and/or or a polytetrafluoroethylene (PTFE). The tissue isolator may have a laminate structure and may include one or more reinforcing layers including, for example, a polyimid, a polyester, Kevlar(R) and/or a polymer such as the M5 fiber manufactured by Magellan Systems International of Arnhem, The Netherlands, for example. Preferably, the tissue isolator will have a high tensile strength (over 1,000 psi) and a high tear resistance. Moreover, the material selected for the tissue isolator will be able to withstand temperatures in excess of about 180 C., for example. However, the tissue isolator 512 may be formed of a material other than specifically enumerated herein while remaining within the spirit of the present invention. Preferably, the shape and size of the tissue isolator 512 are such as to minimize drag on the probe 500 as it is inserted and rotated into the tissue.

Figure 8:
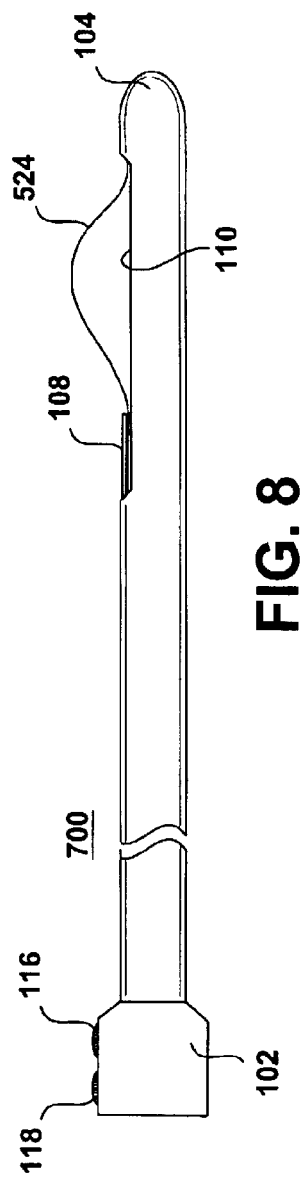
FIG. 8 shows the probe of FIG. 7, in a first extended configuration.
Figure 9:
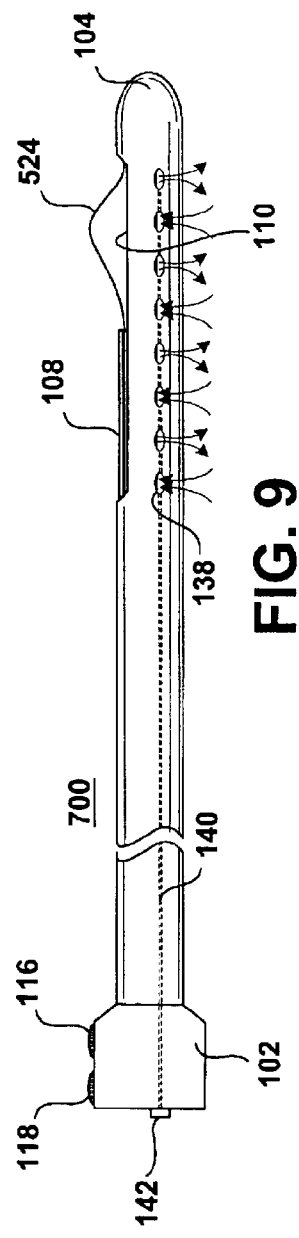
FIG. 9 shows the probe of FIG. 7, in a second extended configuration.

FIGS. 7–9 show an intra-tissue probe 700, according to another embodiment of the present invention. The description of the structures corresponding to reference numbers 102, 118, 116, 114, 112, 108, 110 and 104 is presented above with respect to FIGS. 1–3 and is incorporated herein by reference. Reference numeral 524 corresponds to an RF cutting tool (either monopolar or bipolar) that is configured to selectively bow out of and back into the window 110 defined within the probe 700. The probe cutting tool 524 is electrically coupled to an RF power source 126 such as are known in the art. The probe 700 may be utilized alone, or in combination with a specimen isolator, such as shown at 512 in FIGS. 5A through 6B. According to the present invention, a specimen may be marked as it is being cut or after a partial or complete cut has been made by the tissue-cutting tool 524. Using an RF probe, such as shown at FIGS. 7–9, a soft tissue excisional method, according to the present invention, includes a step of disposing a probe (such as shown at 700) within tissue from which a tissue specimen is to be taken, the probe 700 including an RF tissue cutting tool (such as shown at 524) configured to selectively bow out of and back into a window 110 defined near a distal tip of the probe 700. The probe 700 may then be rotated while RF energy is applied to the RF cutting tool 524. The cutting tool 524 may then be selectively bowed out of the window 110 to cut the specimen from the tissue while the probe 700 is rotated. Selected portions of the surface of the specimen may then be selectively coagulated by the RF cutting tool 524. By judiciously choosing the portions of the surface of the specimen that are coagulated (and/or cauterized), the orientation of the specimen within the body is may be reconstructed after the cut specimen is excised from the body, even if the cut specimen is twisted and/or deformed during retraction thereof from the patient or during subsequent handling. The cutting and marking described above may also be combined with tissue isolation as described relative to FIGS. 5A through 6B and/or with other tissue isolation structures and techniques. As shown in FIG. 9, the body of the probe 700 (and/or the respective probes shown in FIGS. 1–6B) may also define a plurality of through holes 138 in fluid communication with an internal lumen 140 defined within the probe 700. In turn, the internal lumen 140 may be in fluid communication with a proximal port 142 disposed at the proximal end 102 of the probe 700. The through holes 138 may be utilized for the delivery of a fluid to the patient during the cutting, isolating or marking procedure, such as antibiotic agents, analgesic agents or most any pharmaceutical agent. Such agents may be administered to the patient from the port 142. Alternatively, the port 142 may be coupled to suction and the through holes 138 may be utilized to suction out the excisional site of smoke, blood or other bodily fluids during or after the excisional procedure. Alternatively still, more than one port 142 may be provided in the proximal portion 102 and more than one lumen 140 may be defined along the length of the probe 700. The additional lumen may be in fluid communication with selected through holes 138. By this structure, both delivery of a pharmaceutical agent and suctioning may be provided within a single probe 700.

Figures 10A, 10B:
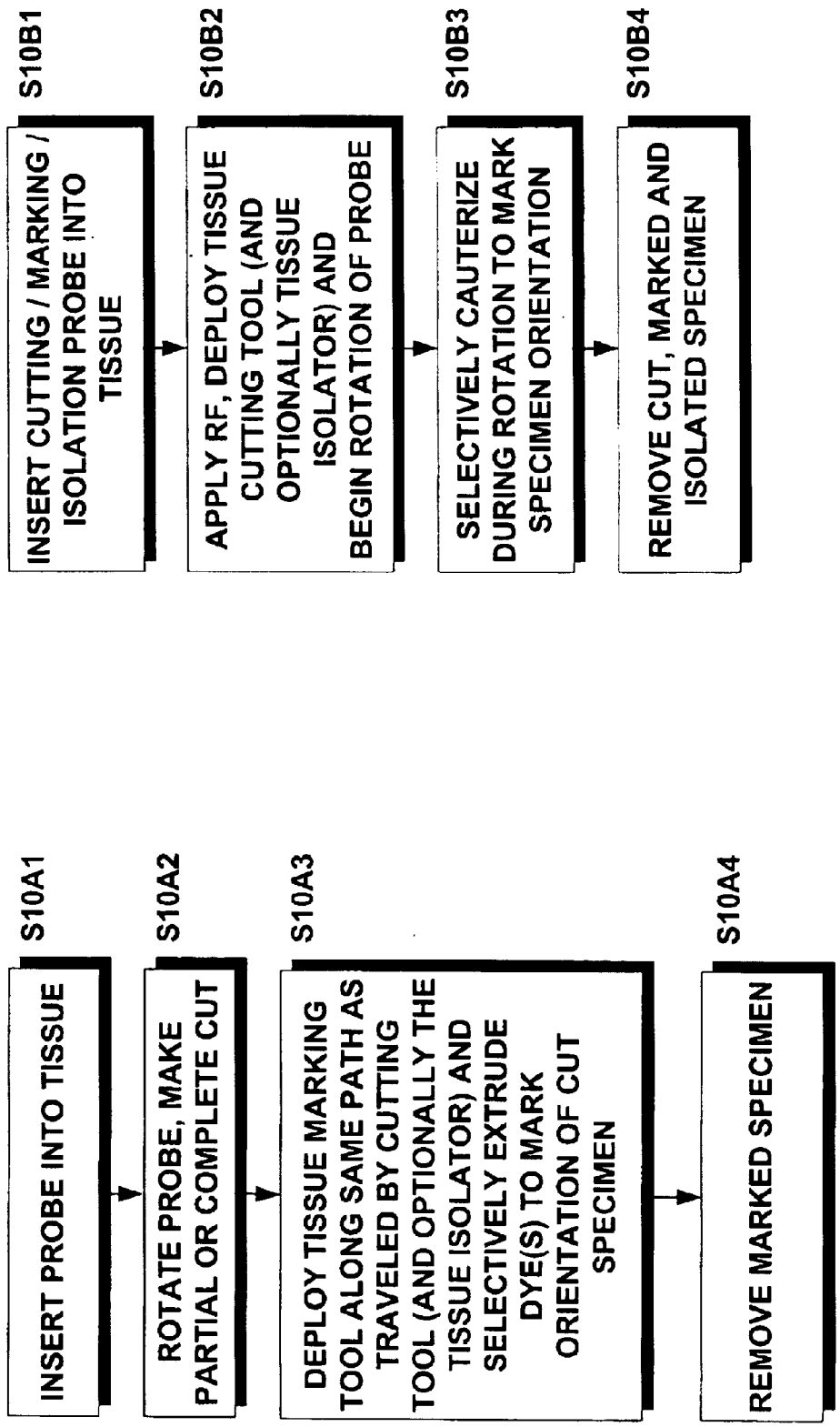
FIG. 10A is a flowchart of a tissue-marking method according to an embodiment of the present invention.
FIG. 10B is a flowchart of a tissue-marking method according to another embodiment of the present invention.

FIGS. 10A and 10B are flowcharts of the excisional, marking and tissue isolation methods according to embodiments of the present invention. Turning first to FIG. 10A, step S10A1 calls for a probe, such as shown in FIGS. 1 through 6B, to be inserted into the patient's soft tissue. For example, a probe such as described herein may be inserted into breast tissue. As shown at S10A2, the probe is then rotated. If the specimen is not already cut from the main tissue mass in which the probe is inserted, a tissue-cutting tool (such as shown at 508 or 524) may be activated and a complete or partial cut of the specimen may be made. Step S10A3 calls for the tissue-marking tool (such as shown at 106 or 514) to be deployed, so that the path taken by the tissue-marking tool 106, 514 follows the path taken by the cutting tool 508, 524. Note that the specimen may be cut by a probe such as shown at 700, after which a tissue-marking specific probe, such as shown at FIGS. 1–3, may be inserted into the soft tissue after retraction of the probe 700 has finished its cut and has been removed. Alternatively, a combination probe, such as shown at FIGS. 6A through 6B may be employed to cut, mark and isolate the specimen. One or more dyes may be extruded from the dye ports 142 to mark the specimen either during the cutting thereof or after the specimen is completely severed from the surrounding tissue. The specimen may be concurrently isolated using the specimen isolator 512 attached to the probe body and the tissue-marking tool 514 or may be isolated after the specimen is completely cut. After the specimen is cut, marked and/or isolated, it may be removed from the patient, by retracting the probe from the excision site and form the patient, as shown at S10A4.

Turning now to FIG. 10B, other embodiments of the present invention call for the insertion of a probe, such as shown at FIGS. 6A through 9 into tissue, as outlined at S10B1. In step S10B2, RF power may be applied to the cutting tool (such as shown at 508, 524) and the cutting tool deployed (i.e., bowed out of window 110) while the probe 500, 700 is rotated, as shown at S10B2. Concurrently, the tissue isolator 512 (if present) may be deployed to isolate the cut tissue from the surrounding tissue. Selected portions of the surface of the partially of fully cut specimen may then be marked by coagulating (or cauterizing) the selected portions using the RF cutting tool 508, 524. The cut, marked and optionally isolated specimen may then be removed from the excision site and the patient by retracting the probe, as outlined in step S10B4.

FIGS. 11–14 each show a representation of a same coagulation-marked tissue specimen 800 in different orientations, according to an embodiment of the present invention. The tissue specimen 800 is shown as marked using one of the probes according to the present invention, as shown in FIGS. 1–9. The tissue specimen 800 defines 6 surfaces: the left superior surface LS best seen in FIG. 11, the right superior surface RS best seen in FIG. 12, the left inferior surface LI best seen in FIG. 13, the right inferior surface RI best seen in FIG. 14, the proximal surface P and the distal surface D hidden in FIGS. 11-14. To reconstruct the orientation of the specimen 800, the physician, according to the present invention, may mark selected portions of the surface of the specimen 800. Using an RF cutting tool 508, 524, for example, the RS surface of the specimen 800 may be marked by coagulating or cauterizing it, in a distinctive pattern such as, for example, two lines. Similarly, selected portions of the LS surface of the specimen 800 may be coagulated or cauterized to create three coagulation or cauterization lines. Likewise, the LI surface thereof may be selectively coagulated or cauterized. In this manner, the original orientation of the specimen 800 may be readily reconstructed, even after the specimen 800 is removed from the patient, twisted and/or otherwise deformed during a pathological examination, for example. To create the lines of coagulation or cauterization shown in FIGS. 11–14, the RF power delivered to the portion of the surface of the cut specimen 800 by the RF cutting tool 508, 524 may be momentarily increased from the power normally applied thereto during the cutting procedure. Preferably however, the coagulating or cauterization is carried out by momentarily maintaining the RF cutting tool 508, 524 immobile or substantially immobile on the selected portion of the surface of the specimen 800 while the RF power delivered to the RF cutting tool 508, 524 is maintained constant. It is to be noted that the pattern of coagulation or cauterization lines shown in FIGS. 11–14 is but an illustrative example, and that other combinations of surfaces of the specimen 800 may be marked (or marked differently than shown in FIGS. 11–14), it being only necessary to distinctively mark a sufficient number of surfaces so as to enable a later reconstruction of the orientation of the specimen 800 within the excision cavity.

FIGS. 15–18 each show a representation of a same dye-marked tissue specimen 900 in different orientations, according to an embodiment of the present invention. As shown therein, selected surfaces of the specimen 900 are marked with a dye, using the marking tool 106 and 514 and the distal port 144, 544 in FIGS. 1–6B. Using the probes 100, 500 of the present invention, dye may be applied to selected surfaces of the specimen 900 so as to enable a ready reconstruction of the orientation thereof after the specimen 900 is removed from the patient. As shown in FIG. 15, the RS and LI surfaces of the specimen 900 may be marked with dye using the marking tool 106, 514. The D surface may be marked with the distal dye port 144, 544. Marking three selected surfaces of the specimen 900 may be sufficient to enable the physician to reconstruct the original orientation of the specimen 900, even of the specimen 900 has been twisted, compressed and/or otherwise deformed after excision thereof from the patient. The dye markings may be of the same or different colors. For example, the dye applied by the marking tool 106, 514 may include any biologically inert dye, such as Methylene Blue, Congo Red and/or Lymphazurin® Blue, for example. The dye may be delivered at a selectable graduated rate to the surface of the specimen 900. For example, the dye may be delivered darker to a first portion of the surface of the specimen 900 and delivered relatively lighter to a second portion of the surface of the specimen 900. Arrows 152, 516 in FIGS. 15 and 17 show the direction of rotation of the tissue-marking tool 106, 514 as it sweeps over the specimen 900. As its sweeps over the surface of the specimen 900 and applies dye to selected surfaces thereof, the dye may become smeared, as shown in FIGS. 15 and 17. The direction of such smearing may provide the physician with yet another indication of the original orientation of the specimen 900 within the excision cavity within the patient. Dye-based markings and coagulation-based markings may be advantageously combined. For example, selected surfaces of a specimen may be marked using coagulation or cauterization, while the distal surface of the specimen may be marked with dye, using the distal dye port 144, 544. Other combinations are possible, and all such combinations are deemed to fall within the scope of the present invention.

Figure 19:
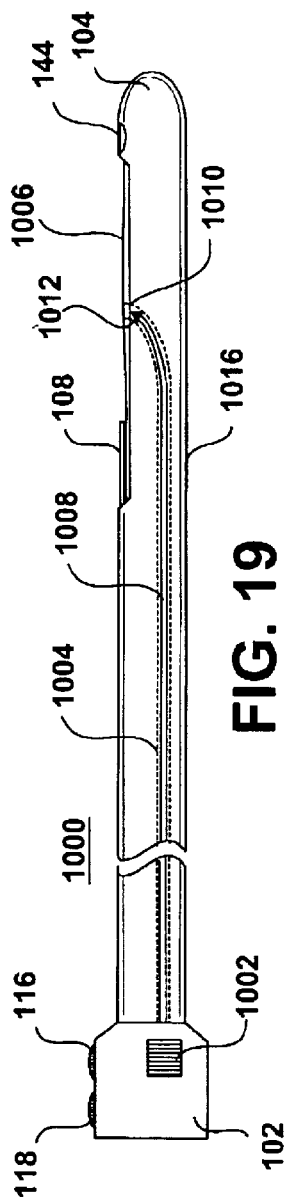
FIG. 19 shows a tissue specimen-stabilizing device, according to an embodiment of the present invention.
Figure 20:
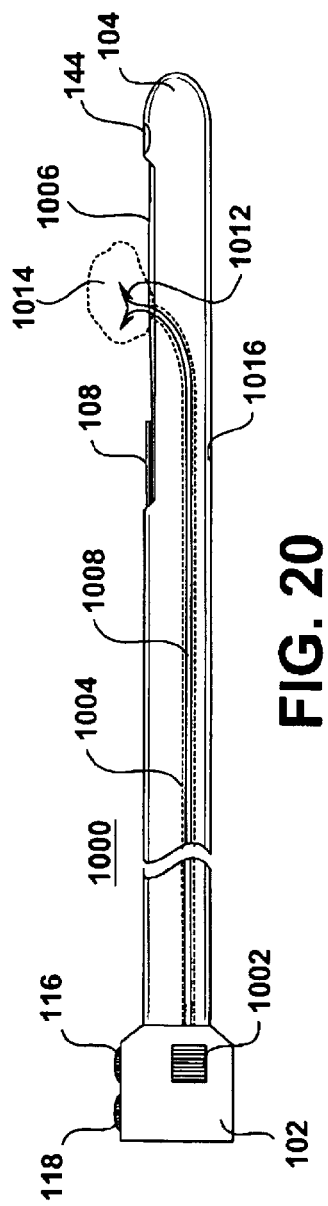
FIG. 20 shows the tissue specimen-stabilizing device of FIG. 19, in which the tissue stabilization tool is shown in a deployed configuration.
Figure 21:
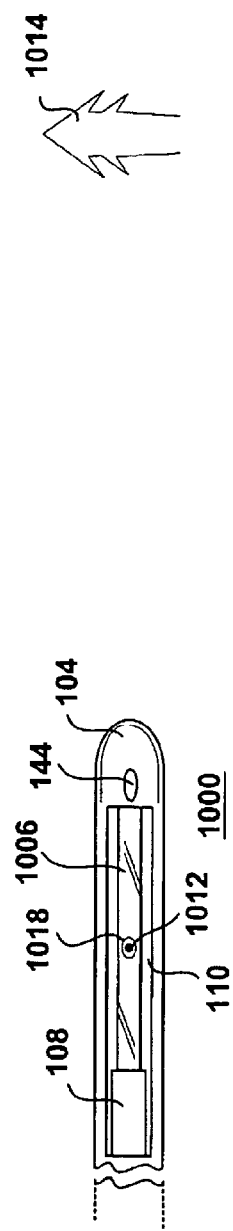
FIG. 21 shows a partial top view of the device of FIGS. 19 and 20.
Figure 22:
FIG. 22 shows another example of the distal barbed tip of the tissue specimen stabilization tool of FIGS. 19–21.

FIGS. 19, 20 and 21 show another embodiment 1000 of the present invention, which allows the orientation of the specimen to be preserved during extraction thereof from the patient. Reference numerals 102, 104, 116, 118, 108 and 144 are structures that correspond to like numbered structures in FIGS. 1–3. The description thereof is, therefore, not repeated here explicitly, but is incorporated herewith by reference. FIGS. 19–21 show a probe 1000 that includes a probe body 1016, the probe body 1016 defining an internal tool lumen 1004 that emerges from the probe body 1016 at a tool port 1010 defined near the distal tip 104 of the probe body 1016. A tool actuator 1002 may be disposed near the proximal end 102 of the probe 1000. The tool actuator 1002 is mechanically coupled to a tissue specimen stabilization tool 1008 disposed within the internal tool lumen 1004. The stabilization tool 1008 may include a barbed tip (such as shown at 1012 or 1014 in FIG. 22, for example). The stabilization tool 1008 is adapted to selectively slide within the tool lumen 1004 and extend out of the tool port 1010 to penetrate and stabilize tissue (such as a cut specimen 1014, for example) adjacent the tool port 1010. As shown in FIGS. 19 and 20, the internal tool lumen 1004 may be generally parallel to a longitudinal axis of the probe body 1016 near the proximal end 102 thereof and may curve away from the axis near the distal tip 104 of the probe body 1016 to emerge at the tool port 1010. The probe 1000 may also include a cutting tool 1006 (an RF cutting tool, for example) disposed near the distal tip 104 of the probe body 1016. The barbed tip 1012 of the stabilization tool 1008 may be configured to expand when it emerges from the tool port 1010. Indeed, FIG. 19 shows the barbed tip 1012 of the stabilization tool 1008 in a folded configuration, whereas FIG. 20 shows the barbed tip 1012 in a deployed configuration. In such a deployed configuration, the barbed tip 1012 hooks into and securely holds the specimen 1014, much like a harpoon. The barbed tip 1012 of the stabilization tool may include or be formed of an elastic material, such as a Nitinol® or similar super elastic alloys, for example. The barbed tip may emerge from the probe 1000 within a hole 1018 defined in the cutting tool 1006 as shown at FIG. 21 or may emerge therefrom adjacent thereto, for example. Other placements of the tool port 1010 are readily envisaged. The barbed tip 1012, 1014 of the stabilization tool 1008 may be shaped as shown in FIGS. 19, 20 or 22. Other designs for the barbed tip 1012, 1014 will occur to those of skill in this art, and all such alternative designs are deemed to fall within the scope of the present invention.

The probes and devices described herein are preferably configured for a single use and are disposable. Alternatively, the probes and devices disclosed herein may be sterilizable and re-usable. Moreover, the probes and devices described herein may be used alone or in combination with other soft tissue excisional systems, such as described in commonly assigned and co-pending application entitled "Excisional Biopsy Devices And Methods" filed on May 4, 2000 and assigned Ser. No. 09/565,611, the disclosure of which is also incorporated herein in its entirety. While the present inventions are well suited to procedures on breast tissue, they are equally well suited to procedures on most any other soft tissue, such as lung tissue, thyroid tissue, liver tissue and/or other tissues.

While the foregoing detailed description has described preferred embodiments of the present invention, it is to be understood that the above description is illustrative only and not limiting of the disclosed invention. Those of skill in this art will recognize other alternative embodiments and all such embodiments are deemed to fall within the scope of the present invention. Thus, the present invention should be limited only by the claims as set forth below.

What is claimed is:

1. An intra-tissue therapeutic device, comprising:
   a probe body, the probe body defining at least one internal dye lumen and a first window near a distal tip of the probe body;
   a tissue-marking tool configured to selectively bow out of and back into the first window, the tissue-marking tool defining at least one dye port in fluid communication with the at least one dye lumen, and
   at least one dye reservoir in fluid communication with the at least one dye lumen.

2. The device of claim 1, wherein the at least one dye reservoir is disposed within the probe body.

3. The device of claim 1, wherein the at least one dye reservoir is external to the probe body.

4. The device of claim 1, wherein the at least one dye reservoir is pre-loaded with a dye.

5. The device of claim 4, wherein the dye includes at least one of Methylene Blue, Congo Red and Lymphazurin Blue.

6. The device of claim 1, wherein the probe body further includes a tissue-cutting tool.

7. The device of claim 6, wherein the tissue-cutting tool is configured to selectively bow out and back into the probe body and wherein the tissue-marking tool is configured to follow in a path of the tissue-cutting tool as the device is rotated.

8. The device of claim 7, wherein the tissue-cutting tool bows out and back into the first window.

9. The device of claim 8, wherein the probe body defines a second window near the distal tip thereof and wherein the cutting-tool is configured to selectively bow out of and back into the second window.

10. The device of claim 6, wherein the cutting tool includes an RF cutting tool.

11. The device of claim 1, wherein the distal tip defines a distal dye port, the distal dye port being in fluid communication with the at least one internal lumen.

12. The device of claim 1, wherein the device is configured for a single use and is disposable.

13. The device of claim 1, further including a distal RF tissue-cutting tool disposed in the distal tip of the probe body.

14. The device of claim 1, further including a specimen isolator coupled to the tissue-marking tool, the specimen isolator being adapted to isolate the specimen from tissue surrounding the specimen.

15. The device of claim 14, wherein the specimen isolator includes a thin flexible film of material, one end thereof being attached to the probe body and another end thereof being attached to the tissue-marking tool.

16. The device of claim 15, wherein the specimen isolator is configured to extend radially from the probe body out of the window when the tissue-marking tool is bowed.

17. The device of claim 15, wherein the material of the tissue isolator may be selected from a group including a polyorganosiloxane, a polydiorganosiloxane, an inorganic elastomer, a silicone elastomer, a teraphthalate, a tetrafluoroethylene, a polytetrafluoroethylene, a polyimid, a polyester, Kevlar® and/or M5®.

* * * * *